United States Patent [19]

Spendlove

[11] 3,976,311
[45] Aug. 24, 1976

[54] TUBING CONNECTOR APPARATUS AND METHOD

[76] Inventor: Ray E. Spendlove, 733 S. 500 West, Vernal, Utah 84078

[22] Filed: Oct. 15, 1974

[21] Appl. No.: 514,360

Related U.S. Application Data

[63] Continuation-in-part of Ser. No. 342,724, March 19, 1973, abandoned.

[52] U.S. Cl. .................................. 285/12; 128/247; 128/295; 128/349 R; 138/89; 285/260; 285/423; 285/DIG. 2
[51] Int. Cl.² ..................... F16L 25/00; F16L 47/00
[58] Field of Search .......... 285/260, 117, 119, 423, 285/DIG. 2, 331, 133 R, 376, 138, 353, 401, 402, 357, 360, 361, 316; 138/89 X; 128/349 R, 349 B, 334 C, 348, 350 R, 247, 295, 283, 349 BV, DIG. 5; 46/88, 90; 220/4 B, 38.5; 339/36, 16

[56] References Cited
UNITED STATES PATENTS

| 725,937 | 4/1903 | Craig ................................ 285/376 X |
| 912,233 | 2/1909 | Dismuth........................... 285/376 X |
| 2,404,052 | 7/1946 | Ginter................................. 285/316 |
| 2,962,688 | 11/1960 | Werner.............................. 339/36 X |
| 3,077,192 | 2/1963 | Berger ................................ 128/283 |
| 3,122,139 | 2/1964 | Jones, Jr. ..................... 128/350 R X |
| 3,372,715 | 3/1968 | Ashton............................. 285/133 R |
| 3,394,954 | 7/1968 | Sarns ............................... 285/423 X |
| 3,396,727 | 8/1968 | Mount................................ 128/349 R |
| 3,633,586 | 1/1972 | Sheridan ..................... 128/349 B X |
| 3,768,476 | 10/1973 | Raitto ............................. 285/423 X |

Primary Examiner—Werner H. Schroeder
Assistant Examiner—Moshe I. Cohen
Attorney, Agent, or Firm—H. Ross Workman; J. Winslow Young

[57] ABSTRACT

A tubing connector having two couplings, each coupling including a central stub tube and a spaced, concentric housing. Each coupling is adapted to be placed on a tubing end with each stub tube in fluid communication therewith. The couplings join to form the connector while the stub tubes telescopically mate to provide fluid communication through the connector and the housings telescopically mate to isolate the mated stub tubes in a spaced enclosure. Each coupling is provided with a closure which includes a cap and a stopper. The stopper seals the stub tube while the cap telescopically mates with the housing to isolate the sealed stub tube in a spaced enclosure. The closures are dimensionally configured to mate while the couplings are mated to form the connector.

13 Claims, 4 Drawing Figures

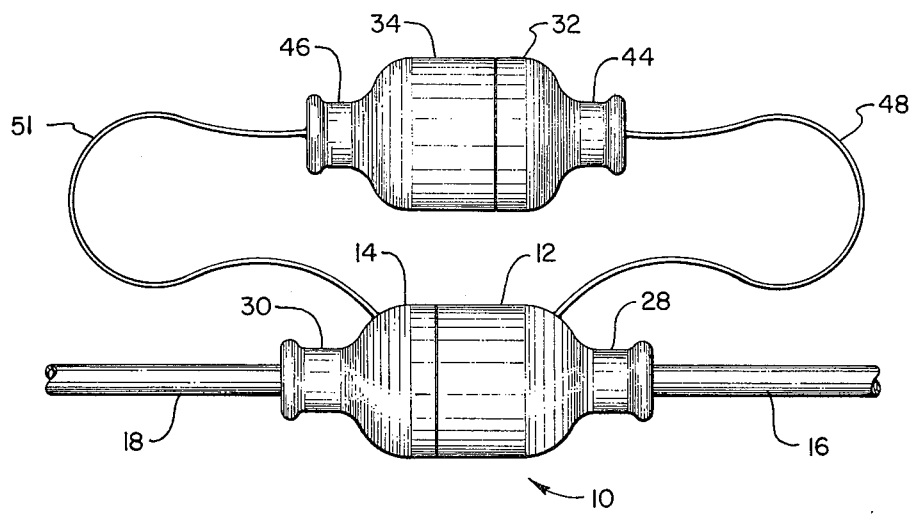
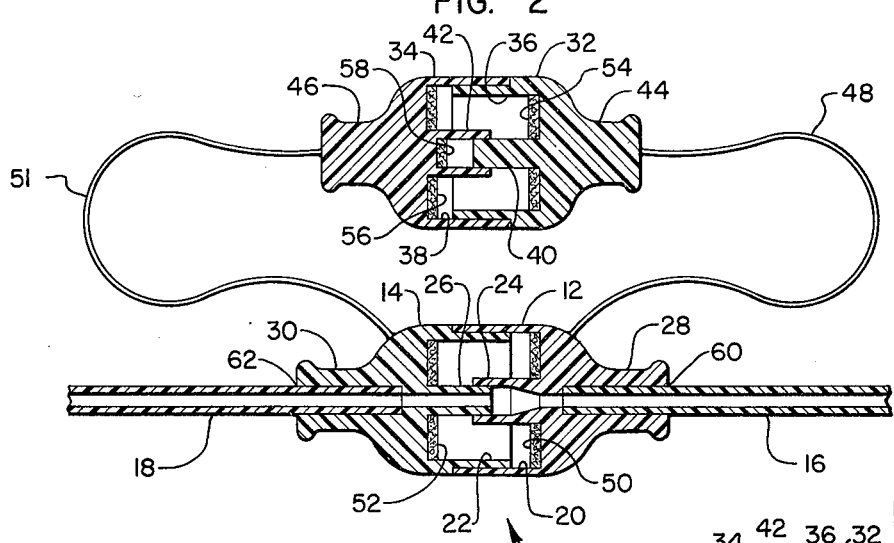
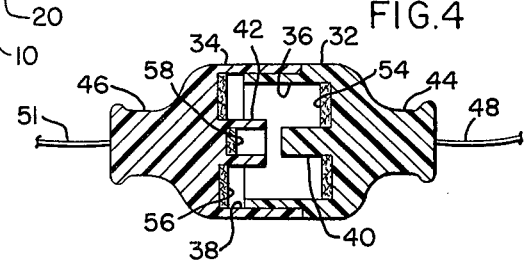
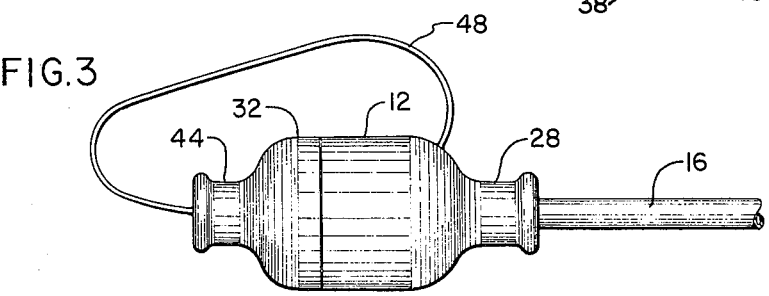

TUBING CONNECTOR APPARATUS AND METHOD

BACKGROUND

1. Field of the Invention

This invention relates to connectors and end caps for tubing. This is a continuation-in-part of my copending application Ser. No. 342,724 filed Mar. 19, 1973 now abandoned.

2. The Prior Art

Various surgical and therapeutic procedures involve the insertion of a fluids-administering/drainage catheter or tubing into a natural or surgically created orifice in a body. Since the interior of the tubing is in direct fluid communication with the body interior, it is of extreme importance that sterility be maintained so as to preclude microbial invasion of the tubing and the body cavity.

An example of such a tubing is a Foley catheter which is used as a drainage catheter for the bladder, the bladder contents being directed to a fluid receiving chamber. Patients undergoing such catheterization frequently require the disconnection of the catheter from the collection chamber. Disconnection has, historically, been accomplished by separating the tubing and clamping or otherwise plugging the upstream end of the tubing with a plug which has been maintained in a sterile solution. The sterile solution is used to minimize contamination of the interior of the catheter by the plug.

Prior art attempts at providing a connector apparatus for tubing ends have been disclosed in U.S. Pat. Nos. 3,484,121; 3,394,954; and 3,768,476. Other patents include U.S. Pat. Nos. 3,633,586 and 3,835,862. None of these patents disclose or suggest a method and apparatus whereby the tubing ends may be joined fluid communication, the joint being isolated within a spaced enclosure. Also they do not disclose how the tubing may be completely separated and each end suitably plugged with the plugged end isolated within a spaced enclosure. Isolation substantially minimizes inadvertent contamination of the tubing ends and plugs.

What is needed is a tubing connector which accommodates interconnection of tubing ends while simultaneously isolating the joint within a spaced enclosure so as to minimize inadvertent contamination of the interior of the tubing, not only during periods of connection, but also during periods when the tubing is disconnected, and the ends plugged and completely separated. Additionally, tubing plugs should be provided with a method and apparatus for minimizing contamination of the tubing plugs both during connection and plugging of the tubing. Such a method and apparatus is disclosed and claimed herein.

BRIEF SUMMARY AND OBJECTS OF THE INVENTION

The present invention includes tubing couplings, each having central stub tubes. The couplings are adapted to be attached on the ends of tubing. Each coupling includes a diametrally enlarged housing about each stud tube. The housing and stub tube of each coupling are adapted to telescopically mate with the housing and stub tube of a corresponding coupling. The mated housings isolate the mated stub tubes in a spaced enclosure.

Each coupling has tethered thereto a closure. The closure has an enlarged cap which telescopically mates with the corresponding housing. The closure also includes a central coaxial plug for plugging the stub tube when the closure is engaged with the coupling. Each closure is also adapted to telescopically mate with a corresponding closure when the couplings are mated, the mated closures thereby isolating the plugs in a spaced enclosure.

It is therefore an object of this invention to provide improvements in connectors for tubing and end plugs therefor.

It is another object of this invention to provide a method whereby tubing may be selectively separated and the ends plugged while simultaneously minimizing contamination of the tubing ends.

Another object of this invention is to provide tubing couplings and end caps therefor which accommodate minimization of contamination of connected and disconnected tubing.

It is even a still further object of this invention to provide a tubing connector wherein fluid communication is provided between two sections of tubing and the tubing joint is maintained in an isolated environment.

These and other objects and features of the present invention will become more fully apparent from the following description and appended claims taken in conjunction with the accompanying drawing.

BRIEF DESCRIPTION OF THE DRAWING

FIG. 1 is an elevation of tubing joined by the connector of this invention, the respective closures for each coupling of the connector being joined in mating relationship.

FIG. 2 is a longitudinal cross section of the embodiment of FIG. 1.

FIG. 3 is an elevational view of one coupling of the connector with the corresponding closure attached.

FIG. 4 is a cross section of a second preferred closure embodiment.

DETAILED DESCRIPTION OF THE PREFERRED EMBODIMENTS

The invention is best understood by reference to the figures wherein like parts are designated with like numerals throughout.

Referring now to FIGS. 1 and 2 the tubing connector is shown generally at 10 and comprises a first coupling 12 and a second coupling 14 which are joined in mating relationship.

Coupling 12 includes a diametrally enlarged housing 20 at one end and a finger grip 28 at the other end. The finger grip 28 includes a central bore 60 which is adapted to receive one end of a tubing 16 in sealing relationship. Fluid communication with tubing 16 through coupling 12 is obtained by a stub tube 24 which is coaxial with housing 20. In this presently preferred embodiment, stub tube 24 is shown having a diametrally enlarged internal diameter so as to telescopically receive the outside diameter of a corresponding stub tube 26 of coupling 14.

Coupling 12 is constructed to provide a spaced annular separation between housing 20 and stub tube 24. This spatial separation prevents accidental contact between the housing and the stub tube, thereby maintaining the aseptic condition of the stub tubes. Additionally, stub tube 24 is recessed from the periphery of housing 20, thereby minimizing contamination of stub 24 during handling.

A flat washer 50 of absorbent material is inserted at the base of the annular space created between housing 20 and stub tube 24. This absorbent material serves to minimize migration of liquid droplets from the interior of stub tube 24 to the periphery of housing 20. Such liquid migration would tend to create an invasion path for microorganisms. If desired, washer 50 may be impregnated with a germicidal agent so as to intercept microorganisms that may traverse the internal surface of the foregoing annular space.

Coupling 14 includes a diametrally enlarged housing 22 at one end and terminates in a finger grip 30 at the other end. Axial bore 62 in finger grip 30 is adapted to receive tubing 18 in sealing relationship. Stub tube 26 is coaxial with housing 22 and completes coupling 14 by providing fluid communication with tubing 18.

Housing 22 of coupling 14 is recessed along a portion of its outer circumference so as to accommodate telescopically mating with housing 20 of coupling 12.

Stub tube 26 is recessed from the periphery of housing 22 to minimize contamination during handling. Stub tubes 26 and 24 are dimensionally configured to accommodate telescopically mating thereby providing fluid communication between tubing 16 and tubing 18.

Coupling 14 also includes a flat washer 52 of absorbent material similarly to washer 50 of coupling 12.

In the presently preferred embodiment of this invention the stub tubes are shown as an integral part of each coupling.

Clearly, each of the stub tubes could be fabricated separately and thereafter joined with a housing to form a coupling. Regardless how fabricated, one important feature of this invention is that the mated stub tubes be isolated in a sealed enclosure so as to minimize contamination.

Coupling 12 has tethered thereto a closure 32, cord 48 serving as the tethering device. Closure 32 includes a diametrally enlarged, cylindrical cap 36 at one end and a finger grip 44 at the other end. Cap 36 includes a coaxial, recessed plug 40 and a flat washer 54 of absorbent material 54 at the base of the annular space between cap 36 and plug 40. Cap 36 is recessed along a portion of its external circumference to accommodate telescopically mating with cap 38 of closure 34.

Closure 34 is tethered to coupling 14 by a cord 51. Closure 34 includes a diametrally enlarged, cylindrical cap 38 at one end and terminates in a finger grip 46 at the other end. A boss 42 is coaxial with cap 38 and is recessed from the periphery of cap 38. Boss 42 includes a concentric blind bore with a diameter which accommodates telescopically mating with either plug 40 or stub tube 26 as will be more fully discussed hereinafter.

A flat washer 56 of absorbent material at the base of the annular space between housing 34 and boss 42 acts in the manner of the other washers. If desired, a disc of absorbent material 58 may also be placed at the base of the blind bore of boss 42.

During periods when coupling 12 is joined to coupling 14 to thereby provide connector 10 for fluid communication between tubing 16 and tubing 18, closure 32 may be joined with closure 34. Joinder of closure 32 with closure 34 isolates the respective tubing stoppers, plug 40 and boss 42, within the annular space created by the telescopically mated caps 36 and 38. Accordingly, contamination of plug 40 and boss 42 is substantially minimized. The stoppers are immediately accessible for each of couplings 12 and 14 and do not require a separate antiseptic solution as in the prior art.

As shown, stub tube plug 40 and boss 42 are configurated to slideably mate, however, it is not an essential feature of this invention that these be mated when closure 32 is mated with closure 34 (see FIG. 4). Preferably, each of plug 40 and boss 42 are recessed from the periphery of caps 36 and 38 so as to reduce accidental contamination of plugs 40 and 42 during all phases of handling.

Examination of the embodiment of FIG. 2 will disclose that closure 32 is dimensionally configured substantially the same as coupling 14 whereas closure 34 is dimensionally configured substantially the same as coupling 12. In this manner, coupling 14 can be replaced with closure 32 and coupling 12 can be replaced with closure 34. Each of closures 32 and 34 mating telescopically with couplings 12 and 14, respectively. Plug 40 seals stub tube 24 whereas boss 42 seals stub tube 26 with each sealed stub tube isolated in the annular space created by its respective housing being closed by the respective cap.

Referring now more particularly to FIG. 3, one-half or one end of connector 10, i.e., coupling 12, is shown as attached to tubing 16 and sealed by closure 32 according to the previously discussed techniques. Cord 48 has thereby served to tether closure 32 to coupling 12. The cords also serve as guides for the person manipulating the closures to place the correct closure upon its corresponding coupling.

Finger grips 28 and 44 assist in the handling of this device by providing a secure gripping portion for the operator, thereby minimizing inadvertent contamination of the device. Although the aforementioned finger grips are useful, the connector and closure device of this invention may dispense with the same. However, it is currently believed that these finger grips are useful since each of the couplings 12 and 14 and the closures 32 and 34 are specifically designed to slideably mate in a snug pressfit relationship. Accordingly, the separation and joinder of the respective couplings and closures will require a significant force exerted thereon in order to affect the appropriate condition.

The Method

The apparatus of the present invention greatly assists the method herein of minimizing contamination of tubing while simultaneously permitting ease of connection, separation and closure. According to the presently preferred embodiment of this invention, a tubing, for example, a Foley catheter, may be prepared from two tubing segments 16 and 18. One end of each segment of tubing 16 and 18 has placed upon it a coupling 12 and 14, respectively.

In the presently preferred embodiment of this invention, a seal is achieved between couplings 12 and 14 and tubing 16 and 18, respectively, for example, by using any suitable adhesive material which may be placed in bores 60 and 62 to assist in the sealing and thereby achieve a fluid tight seal between the respective tubing and its coupling. The connector 10 may be interposed into the tubing at the hospital, either by severing the tubing and inserting the connector or for joining additional lengths of tubing. Connector 10 may also be suitably interposed into a length of tubing during manufacture.

After connection with connector 10, combined tubing 16 and 18 may be used as a catheter, for example, by insertion of one end of tubing 16 into the bladder of a patient undergoing treatment, insertion being accomplished according to standard procedures. Connector 10 maintains a fluid tight joint between tubing 16 and 18 so as to direct the bladder contents to a suitable receptacle such as a collection reservoir (not shown). If it is now desired that the patient be ambulatory and to be disconnected from the collection reservoir (not shown) either the patient or appropriate medical personnel may simply uncouple connector 10 and close each of the respective couplings 12 and 14 with closures 32 and 34, respectively. The patient may then be ambulatory or moved about in a wheelchair or the like and still retain the catheter within the bladder with the small profile of tubing 16, coupling 12 and closure 32 concealed by the clothing of the patient.

Since tubing 16 is now plugged and the plug isolated in a sealed environment, the patient is able to bathe or otherwise cleanse his body without subjecting the plugged end of tubing 16 to inadvertent contamination. After completion of the necessary personal functions, the patient may then suitably remove closure 32 from coupling 12 and rejoin coupling 14 with coupling 12 and closure 34 with closure 32 as previously discussed and set forth.

While the patient has tubing 16 closed by closure 32 placed on coupling 12, coupling 14 is closed by closure 34, although this latter condition is not shown herein for sake of simplicity. If it were shown, this would be substantially a mirror image of FIG. 3.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A tubing connector comprising:
   a first coupling comprising:
      a diametrally enlarged, cylindrical first housing having an open end and a closed end;
      a first stub tube coaxial with the housing, the first stub tube being integral with the housing and providing fluid communication through the closed end of the first housing; and
      means accommodating attachment of the first coupling to one fluid conduit so as to provide fluid communication between the one fluid conduit and the first stub tubing;
   a second coupling comprising:
      a diametrally enlarged, cylindrical second housing having an open end and a closed end, the second housing accommodating matingly at its open end the open end of the first housing to thereby provide a sealed enclosure;
      a second stub tube coaxial with the second housing, the second stub tube being integral with the second housing and providing fluid communication through the closed end of the second housing; and
      means accommodating attachment of the second coupling to another fluid conduit so as to provide fluid communication between the other fluid conduit and the second stub tube; and
   the first housing and first stub tube of the first coupling being dimensionally configurated to telescopically mate with the second housing and second stub tube of the second coupling, respectively, the mated stub tubes providing fluid communication between the first and second tubing ends and the mated first and second housings isolating the mated stub tubes in a sealed, diametrally spaced annular enclosure.

2. A tubing connector as defined in claim 1 wherein each coupling has tethered thereto a closure, each closure comprising a diametrally enlarged cap and a coaxial stopper within the cap, the closures being dimensionally configurated to telescopically mate with the corresponding coupling to which it is tethered.

3. A tubing connector as defined in claim 2 wherein each closure has a planar annulus of absorbent material circumscribing the base of the stopper.

4. A tubing connector as defined in claim 3 wherein the absorbent material is impregnated with a germicidal agent.

5. A tubing connector as defined in claim 2 wherein the stoppers are adapted to telescopically mate when the caps of the closures are mated.

6. A tubing connector as defined in claim 2 wherein the stoppers are recessed within the caps and do not mate when the caps of the closures are mated.

7. A tubing connector as defined in claim 1 wherein each stub tube is recessed within each respective housing so as to substantially minimize accidental contamination of the stub tubing when the couplings are uncoupled.

8. A tubing connector as defined in claim 1 wherein a planar annulus of absorbent material is placed in each coupling around the base of the stub tube.

9. A tubing connector as defined in claim 8 wherein the absorbent material is impregnated with a germicidal agent.

10. A tubing connector comprising:
   a first coupling comprising a diametrally enlarged housing, a coaxial first stub tube within the housing, the coupling having an axial bore accommodating attachment of the first coupling to one fluid conduit so as to provide fluid communication between the one fluid conduit and the first stub tube;
   a second coupling comprising a diametrally enlarged housing, a coaxial second stub tube within the housing, the second coupling having an axial bore accommodating attachment of the second coupling to one other fluid conduit so as to provide fluid communication between the other fluid conduit and the second stub tube, each of the couplings having an annular space separating the stub tube from the housing;
   a first closure tethered to the first coupling and comprising a cap mateable with the first housing and a coaxial stopper within the cap, the stopper being adapted to plug the first stub tube; and
   a second closure tethered to the second coupling and comprising a cap mateable with the second housing and a coaxial stopper within the cap, the stopper being adapted to plug the second stub tube, the first and second closures having dimensionally configurated housings which telescopically mate.

11. A tubing connector as defined in claim 10 wherein each of the housings form an annular space about each stub tube and a planar, annulus of absorbent material is disposed in the annular space about the base of each stub tube.

12. A tubing connector as defined in claim 10 wherein each of the caps forms an annular space about each stopper and a planar, annulus of absorbent material is disposed in the annular space about the base of each stopper.

13. A method for accommodating joinder and separation of first and second conduits while minimizing contamination, comprising the steps of:

obtaining first and second conduits, an end of the first conduit being joined in fluid communication with an end of the second conduit through a connector comprising a first and a second coupling;

affixing a first coupling to the end of the first conduit and a second coupling to the end of the second conduit, each coupling comprising a diametrally enlarged housing coaxial with a diametrally reduced stub tube;

mating the stub tubes to provide fluid communication between the first and second conduits through the mated stub tubes while simultaneously isolating the mated stub tubes in a diametrally spaced enclosure formed by telescopically mating the housings; and tethering a closure to each of the couplings, each closure having a diametrally enlarged cap which is dimensionally configured to telescopically mate with the other cap, each cap also being dimensionally configured to telescopically mate with the housing of the coupling to which it is tethered, each closure having a coaxial plug within the cap for sealing the respective stub tube when the closure is mated with the coupling.

* * * * *